US011703505B2

(12) United States Patent
Nahm et al.

(10) Patent No.: US 11,703,505 B2
(45) Date of Patent: Jul. 18, 2023

(54) NANO-DYNAMIC BIOSENSOR AND FABRICATION METHOD THEREFOR

(71) Applicant: KOREA RESEARCH INSTITUTE OF STANDARDS AND SCIENCE, Daejeon (KR)

(72) Inventors: Seung Hoon Nahm, Daejeon (KR); Nam Hee Lee, Daegu (KR); Kwon Sang Ryu, Daejeon (KR); Un Bong Baek, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 166 days.

(21) Appl. No.: 16/622,175

(22) PCT Filed: May 31, 2018

(86) PCT No.: PCT/KR2018/006204
§ 371 (c)(1),
(2) Date: Mar. 17, 2020

(87) PCT Pub. No.: WO2018/230871
PCT Pub. Date: Dec. 20, 2018

(65) Prior Publication Data
US 2020/0225221 A1 Jul. 16, 2020

(30) Foreign Application Priority Data
Jun. 12, 2017 (KR) ........................ 10-2017-0072938

(51) Int. Cl.
*G01N 33/551* (2006.01)
*G01N 29/02* (2006.01)
(Continued)

(52) U.S. Cl.
CPC ......... *G01N 33/551* (2013.01); *G01N 29/022* (2013.01); *G01N 29/036* (2013.01); *H01L 29/1606* (2013.01)

(58) Field of Classification Search
CPC .. G01N 33/551; G01N 29/022; G01N 29/036; G01N 33/544; G01N 2291/0255;
(Continued)

(56) References Cited

U.S. PATENT DOCUMENTS 7,884,324 B2 * 2/2011 Blick .................... H01J 29/023 250/310
2004/0135144 A1 * 7/2004 Yamada ................. H03H 9/588 257/59
(Continued)

FOREIGN PATENT DOCUMENTS

KR 10-2007-0072224 A 7/2007
KR 10-2010-0001062 A 1/2010
(Continued)

OTHER PUBLICATIONS

Korea Research Institute of Standards and Science, "Development of Multi-mode Sensing Technology for Harmful Substance based on Nano-web" including English Summary, The Fusion Research Program for Green Technology—252 pages (2016).
(Continued)

*Primary Examiner* — Melanie Brown
(74) *Attorney, Agent, or Firm* — Knobbe, Martens, Olson & Bear, LLP

(57) ABSTRACT

The present invention relates to a nano-dynamic biosensor and a fabrication method therefor. A biosensor according to the present invention comprises a substrate having a hollow structure and a graphene layer formed thereon wherein a probe material is bound to the surface of the graphene layer and the resonance vibration of the hollow structure formed
(Continued)

in the substrate is modulated as the probe material increases in weight when a target material to be detected is coupled to the probe material without being labeled, whereby the biosensor is expected to take advantage of the modulation to measure the coupling of the target material including vaccinia virus with high sensitivity on a femtogram ($10^{-15}$ g) level.

6 Claims, 3 Drawing Sheets

(51) Int. Cl.
*G01N 29/036* (2006.01)
*H01L 29/16* (2006.01)

(58) Field of Classification Search
CPC ....... G01N 2291/0256; G01N 2333/07; G01N 29/12; G01N 33/54373; G01N 2333/005; H01L 29/1606
See application file for complete search history.

(56) References Cited

U.S. PATENT DOCUMENTS

2005/0074871 A1* 4/2005 Albert .............. C12Q 2523/307 435/287.2
2010/0317124 A1 12/2010 Kim et al.
2011/0101365 A1* 5/2011 Kim ....................... H10K 85/20 257/66
2013/0062104 A1* 3/2013 Craighead ............. B81B 3/0094 174/255
2013/0258552 A1* 10/2013 Choi ...................... B82Y 40/00 977/734
2013/0309776 A1* 11/2013 Drndic ............. G01N 33/48721 436/94
2014/0130972 A1* 5/2014 Ren ....................... C01B 32/184 156/249
2014/0305191 A1* 10/2014 Schmid .................. G01N 9/002 73/24.03
2015/0309073 A1* 10/2015 Mirkin ................... G01Q 70/14 850/55
2016/0123973 A1* 5/2016 Cubukcu .............. G01N 29/036 506/9
2017/0021344 A1* 1/2017 Hau ......................... C12N 9/96

FOREIGN PATENT DOCUMENTS

KR 10-2017-0048896 A 5/2017
KR 20170048896 * 5/2017

OTHER PUBLICATIONS

International Search Report of corresponding PCT Application No. PCT/KR2018/006204—4 pages (dated Oct. 15, 2018).

* cited by examiner

【Fig. 1】
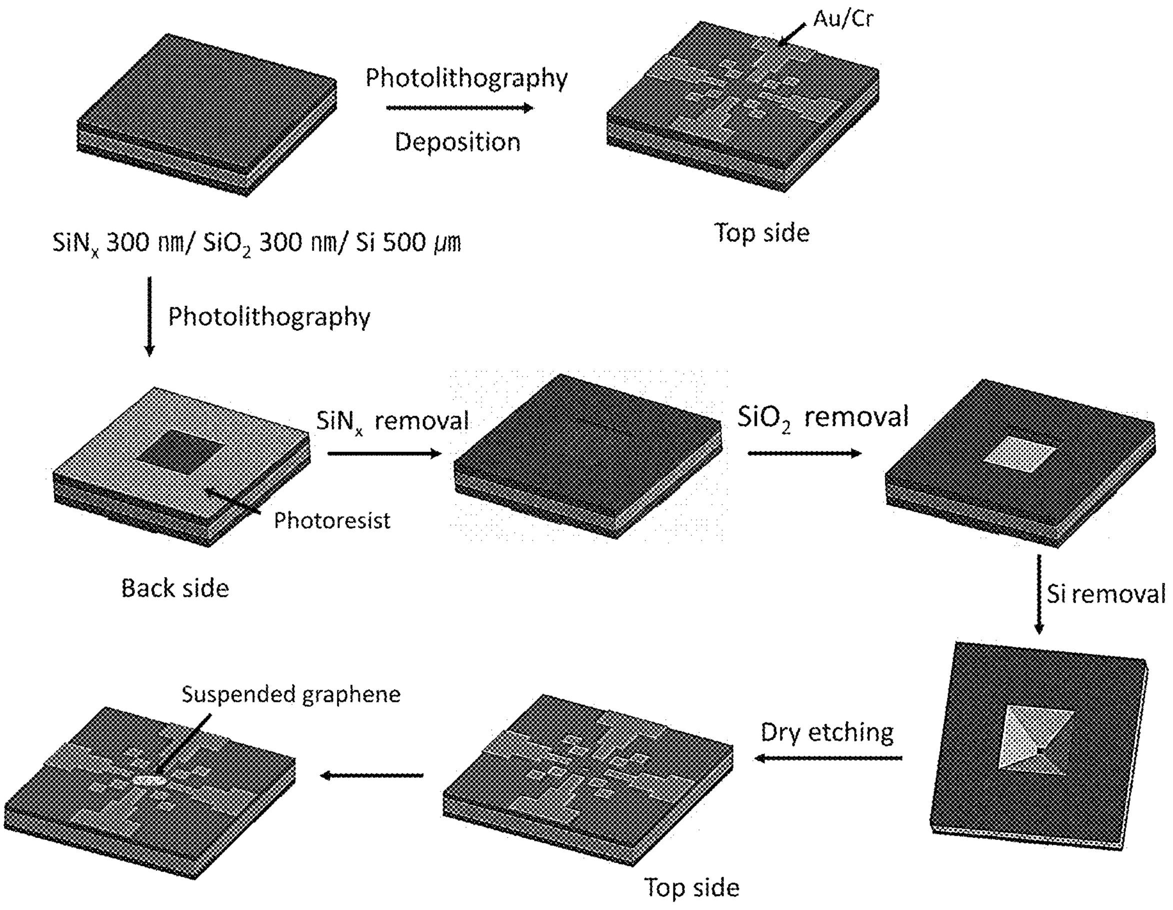

【Fig. 2】
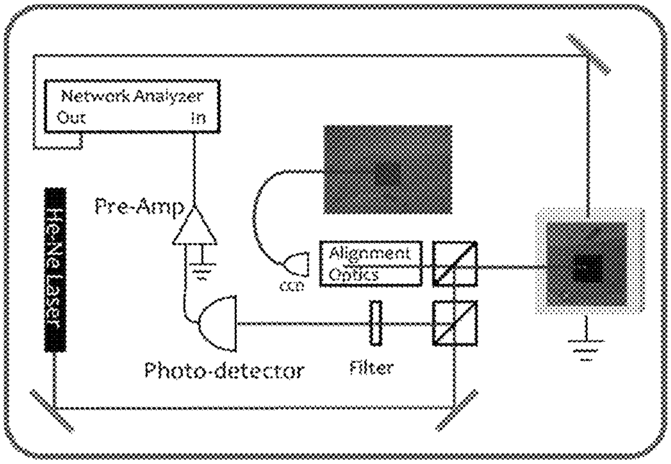
【Fig. 3】
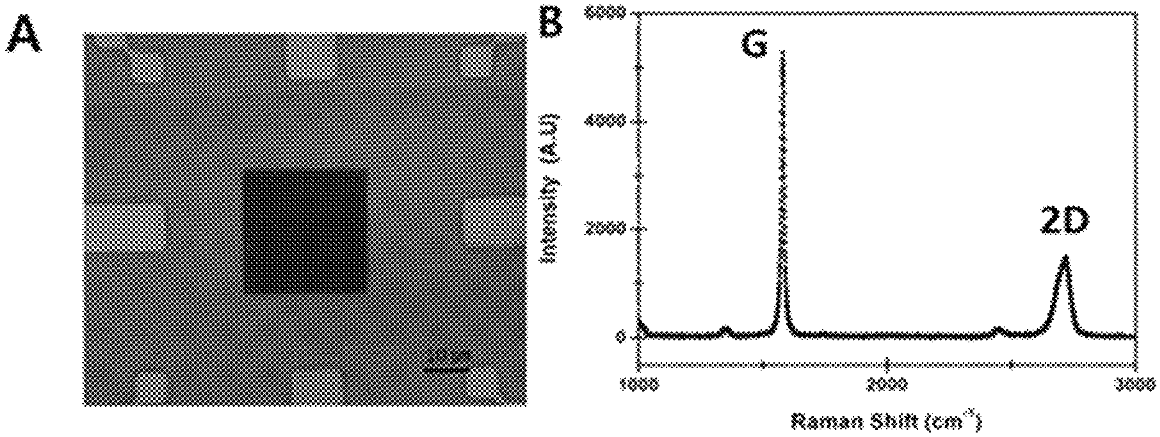

【Fig. 4】
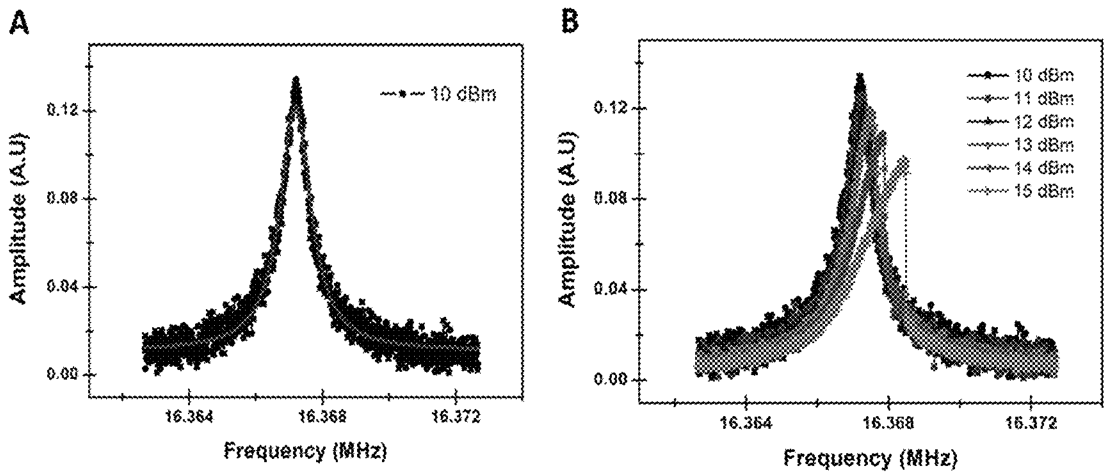
【Fig. 5】
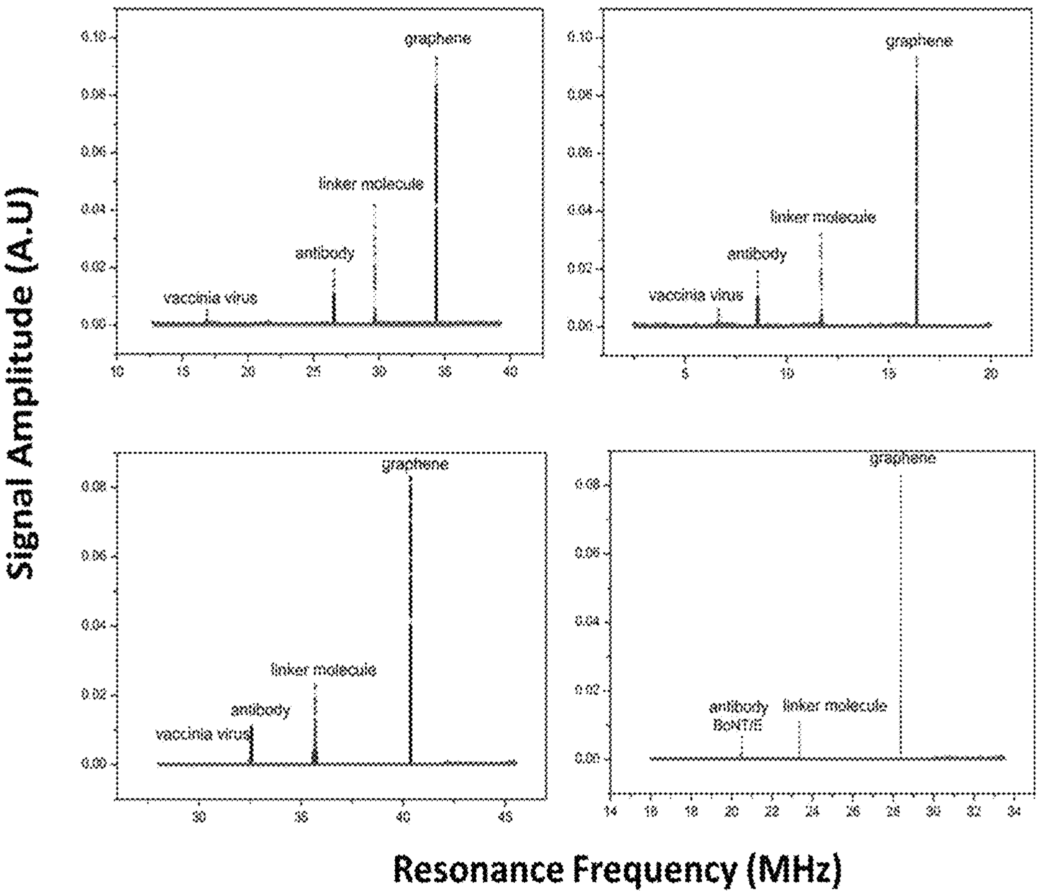

NANO-DYNAMIC BIOSENSOR AND FABRICATION METHOD THEREFOR

TECHNICAL FIELD

The present invention relates to a nano-dynamic biosensor and a fabrication method therefor.

BACKGROUND ART

A detection of biomaterials has been an attractive research field for researchers over a long period of time, and the importance of the detection of biomaterials in biological and medical fields has recently increased greatly. As a result, various methods have been developed through various attempts to qualitatively or quantitatively detect the biomaterials.

There are two main methods for detecting biomaterials depending on whether to use a marker. Firstly, the non-marker method uses a target material that has not been subjected to any treatment, and when a dynamic sensor using the non-marker method uses established semiconductor technology, the non-marker method is the preferred method for batch production of hundreds of nano-dynamic system arrays. The dynamic sensor that is sensitive to changes in vibrations or deformations according to molecular adsorption has been completed through advances in micro and/or nanotechnology. As the size of the nano-dynamic biosensor decreases, the nano-dynamic biosensor has significantly improved mass resolution. The nano-dynamic system may exhibit very low mechanical suitability for converting biomolecular recognition events into measurable displacements. Since a size of the biomolecule is compared with a dimension of the mechanical system, the nano-dynamic system is sensitive to mechanical properties.

The nano-dynamic system set to vibrate at natural frequencies performs the same function as a precise mass sensor. As a physical size of the nano-dynamic system decreases, mass sensitivity of a nano-dynamic resonator is improved, but the physical size of the nano-dynamic system is inversely proportional to a mass of a device.

A resonator fabricated by top-down technology has proven to have a detection limit in zeptogram ($10^{-21}$ g), and a nano-mechanical sensor assembled in semiconductor nano-wire, carbon nanotube (CNT), or the like that is fabricated by bottom-up technology has approached a detection limit up to yoctogram ($10^{-24}$ g). A result of detecting a single cell and molecules of femtogram ($10^{-15}$ g) as well as disease marker proteins such as prostate-specific antigen (PSA), C-creative protein (CRP), or myoglobin by a method for detecting molecules using a change in cantilever defection or a resonance frequency shift has been reported. There is also an example showing that a thin silicon cantilever resonator can be effectively used for microbial detection.

A mass sensing resonator as described above is based on a resonance frequency sensitive to a change in an attached mass, and the frequency shift according to the contacted mass is affected by a position of the attached mass. In this respect, graphene is very effective for detecting adsorbed molecules because the graphene can provide a larger surface area exposed compared to carbon nanotubes having circular geometry and poor interfacial interaction. In addition, the graphene has a form of a two-dimensional structure, and therefore is used for a mechanical resonator and an atomic dust-detecting device for mass sensing. However, the graphene in mass sensors has been studied in a limited range. As an example, the Sakai-Pur group used molecular structural dynamics to analyze vibrational behavior of graphene having a point mass at a center of a sheet, and found that a shifted value at a fundamental frequency is independent of chirality and an aspect ratio. In addition, Wong group also performed nano-mechanical characterization of graphene structures by atomic-force microscopy (AFM) to measure electrostatic deflection, and showed that a small size and a high operating frequency of the graphene structure is very promising for resonant mass sensing applications. Sun and Liu have analyzed a vibration frequency of a monolayer or multilayer graphene sheet and studied the responsiveness and sensitivity of graphene-based mass sensors based on classical continuum theory

DISCLOSURE

Technical Problem

An object of the present invention is to provide a biosensor capable of detecting a fine change in a mass using a modulation in resonance vibration of a hollow structure formed under graphene according to an increase in weight when a probe material is coupled to a target material without labeling the target material detected by using, as the graphene, a member to which the probe material is coupled and forming a graphene layer on the hollow structure.

Technical Solution

In one general aspect, a biosensor includes:

a support portion configured to include an insulating substrate having a hollow structure;

a resonance unit configured to include a functional group on a graphene surface, including a monolayer or multilayer graphene layer that is stacked on the hollow structure of the support portion;

a detection unit configured to be disposed on the resonance unit in combination with the functional group; and a measurement unit configured to be disposed to measure a change in weight of the detection unit.

In another general aspect, a fabrication method for a biosensor includes:

applying a photoresist on an insulating substrate;

exposing a first surface of the insulating substrate, etching the photoresist, and then forming an electrode;

forming a pattern for manufacturing a membrane on a second surface of the insulating substrate;

forming the membrane on the first surface by an etching process and solvent treatment on the second surface of the insulating substrate;

removing the formed membrane;

stacking a graphene layer on the hollow structure formed at a portion from which the membrane of the first surface is removed;

forming the resonance unit by treating a surface exposed to an outside of the graphene layer with a surface treatment agent containing the functional group; and coupling the detection unit to the resonance unit including the functional group.

Advantageous Effects

The biosensor according to the present invention includes a substrate having a hollow structure and a graphene layer formed thereon wherein a probe material is bound to the surface of the graphene layer and the resonance vibration of the hollow structure formed in the substrate is modulated as the probe material increases in weight when a target material to be detected is coupled to the probe material without being labeled, whereby the biosensor is expected to take advantage of the modulation to measure the coupling of the target material including vaccinia virus with high sensitivity on a femtogram ($10^{-15}$ g) level.

BRIEF DESCRIPTION OF THE DRAWINGS

FIG. 1 is a graph of a fabrication process of a suspended graphene-based nano-dynamic device.

FIG. 2 is a schematic diagram of measurement of dynamic properties of a nano-dynamic system.

FIG. 3 shows a) a diagram showing an optical image of a suspended graphene-based nano-dynamic devices, and b) a diagram showing Raman c measurement results of suspended graphene.

FIG. 4 shows a) a graph showing a nano-dynamic device whose resonance frequency is about 16.367 MHz and Q-factor is about 14,613 and a result of Lorentzian fit represented by a red solid line, and b) a graph showing a measurement result of the nano-dynamic device according to a change in driving strength.

FIG. 5 shows a) a diagram showing a result of checking a detection of vaccinia virus at a concentration of $10^8$ PFU, b) a diagram showing a result of checking a detection of vaccinia virus at a concentration of $10^5$ PFU, c) a diagram showing a result of checking a detection of vaccinia virus at a concentration of $10^3$ PFU, using the nano-dynamic device, and d) a diagram showing a related result of a control group in which a detection of 1 μM BoNT/E antibody is checked.

BEST MODE

Hereinafter, a nano-dynamic biosensor and a fabrication method therefor according to an exemplary embodiment of the present invention will be described in detail with reference to the accompanying drawings.

The drawings to be provided below are provided by way of example so that the spirit of the present invention can be sufficiently transferred to those skilled in the art. Therefore, the present invention is not limited to the accompanying drawings provided below, but may be modified in many different forms. In addition, the accompanying drawings suggested below will be exaggerated in order to clear the spirit and scope of the present invention.

Technical terms and scientific terms used in the present specification have the general meaning understood by those skilled in the art to which the present invention pertains unless otherwise defined, and a description for the known function and configuration unnecessarily obscuring the gist of the present invention will be omitted in the following description and the accompanying drawings.

Further, in the present invention, when a layer is described as "on" another layer or a substrate, the layer may be present in direct contact with another layer or the substrate, or may present in contact therewith with a third layer interposed therebetween.

Vaccinia virus is a bovine-host virus, and has been used as a vaccine against smallpox. Smallpox virus is a virus that can be directly transmitted between humans and can occur anywhere in the world. In addition, once the smallpox outbreaks, there is no cure for the smallpox, and only an extremely limited amount of vaccination liquid against the smallpox is available.

Therefore, the smallpox virus is one of the most powerful viruses that can be used for bioterrorism. With the increasing risk of terrorism around the world, it is considered that the smallpox virus, which is already considered to be extinct on earth, can be used as a terrorist weapon. Accordingly, the vaccinia virus has been studied as an alternative material to the smallpox virus. The vaccinia virus consists of 190 kbp double-stranded DNA and consists of 250 genes. The mature virus has a size of about 360 nm×270 nm×250 nm, and a mass of about 5 to 10 femtograms (fg, $10^{-15}$ g).

An aspect of the present invention provides a biosensor including:

a support portion configured to include an insulating substrate having a hollow structure;

a resonance unit configured to include a functional group on a graphene surface, including a monolayer or multilayer graphene layer that is stacked on the hollow structure of the support portion;

a detection unit configured to be disposed on the resonance unit in combination with the functional group; and a measurement unit configured to be disposed to measure a change in weight of the detection unit.

In the present invention, a material of the insulating substrate is not particularly limited as long as the material does not hinder the object of the present invention, but the material may preferably include III-V compound semiconductors, such as Si, GaAs, InP, and InGaAs, glass, an oxide thin film, a dielectric thin film, a metal thin film, and the like may be included, but is not limited thereto. Preferably, the substrate may include a silicon substrate, and more preferably, a silicon substrate having an insulating film formed on a surface thereof. For example, as the insulating substrate, an insulating substrate in which a silicon oxide layer and a $SiN_x$ layer (x is a real number between 1 and 5) are formed on the surface thereof may be used, and more preferably, an insulating substrate in which a silicon dioxide ($SiO_2$) layer and a silicon nitride ($Si_3N_4$) layer are sequentially stacked on the surface thereof and an insulating film is formed on the surface thereof may be used. When the above insulating substrate is used, the nano-dynamic device can improve sensitivity to a change in mass.

In the present invention, the size of the hollow structure is not particularly limited when the hollow structure has an inner area completely applied by the graphene layer in a range in which the object of the present invention for utilizing graphene as a device is not hindered. However, when the hollow structure has the inner area smaller than 26 μm×26 μm, the size of the hollow structure is not particularly limited, but preferably the hollow structure having a size of $1.0\times10^1$ $\mu m^2$ to $6.5\times10^2$ $\mu m^2$, and more preferably $1.0\times10^2$ $\mu m^2$ to $6.4\times10^2$ $\mu m^2$ can be used, and most preferably, the hollow structure having a size of $6.0\times10^2$ $\mu m^2$ to $6.3\times10^2$ $\mu m^2$. Not only can the multilayer graphene be easily attached to the hollow structure in the above range, but the Q-factor of the device can also have a value between $10^4$ and $10^5$ which is a high range of the ranges that semiconductors generally have. As a result, the multilayer graphene can be used as a sensor having high sensitivity, which is preferable.

Since graphene, which belongs to carbon nanomaterials, has high mobility, low electrical noise (1/f noise), and a two-dimensional structure in which all carbon atoms are exposed to the atmosphere, the graphene has a very wide surface area compared to the existing organic/inorganic materials, and as a result, can maximize the sensitivity of the sensor when applied to the sensor. In addition, when the graphene having the two-dimensional structure is subjected to a lithography process to be made into an element, the graphene can be more easily and conveniently surface-functionalized than other 0-dimensional or 1-dimensional structures having a large surface area, and the graphene can be driven even with low power consumption due to excellent electrical characteristics of the graphene.

Examples of the graphene may include, but is not limited to, graphene mechanically exfoliated from graphite, graphene chemically exfoliated from graphite, graphene chemically synthesized from a carbon source, graphene synthesized from a SiC substrate, and the like.

In the present invention, the graphene may be a platform of the sensor element by the patterning process. The patterning process may include, but is not limited to, reactive ion etching (RIE), photolithography, electron-beam lithography, scanning probe lithography, laser-induced direct patterning, block copolymer lithography, nanoimprint lithography, photocatalytic etching, plasma etching processes, and the like.

A metal electrode may be deposited by at least one selected from electron-beam evaporation deposition, thermal evaporation deposition, laser molecular beam epitaxy (L-MBE), pulsed laser deposition (PLD), electro-plating, and sputtering, but the deposition method is not limited thereto.

The patterning in the present invention is not limited at a level that does not hinder the object of the present invention, and may be carried out using any suitable lithography process, for example, any one or two or more selected from the group consisting of photolithography, electron-beam lithography, ion-beam lithography, EUV lithography, and x-ray lithography, but may be preferably carried out using photolithography.

In the present invention, the kind of the functional groups is not particularly limited within a range in which the object of the present invention is not hindered, but it is preferable to use at least one selected from the group consisting of $—NH_2$, —COOH, —CHO, —OH, and pyrene, and it is more preferably to use a pyrene structure as a linker molecule since biomolecules are easily recognized and binding property is increased due to the structural characteristics of the pyrene.

In the present invention, the kind of the detection unit is not limited as long as the detection unit can come into contact with the target material, but the detection unit may be preferably selected from the biomolecules, and more preferably any one or two or more selected from the group consisting of DNA, antigens, antibodies, and peptides, but it is preferable to use the antibody for the detection of the antigen. For example, for the detection of the antigens such as the vaccinia virus, it is most preferable to use the vaccinia virus antibodies in order to increase the sensitivity of the sensor.

In the present invention, the configuration of the detection unit is not particularly limited as long as the detection unit does not hinder the object of the present invention in its characteristics, but the detection unit preferably includes a probe material, in which the probe material is bound to the target material to be detected to increase the weight, and it is preferable to use a material capable of checking the binding between the target material and the probe material by a modulation of a natural frequency of the hollow structure in that the biosensor is implemented to selectively detect the biomaterial with high sensitivity.

In the present invention, when the target material and the probe material are pairs that can selectively be bound, the kind of the pairs is not limited, but using the antigen and the antibody each can significantly improve the detection result of the vaccinia virus.

Another aspect of the present invention provides a method for fabricating a biosensor including:

applying a photoresist on an insulating substrate;

exposing a first surface of the insulating substrate, etching the photoresist, and then forming an electrode;

forming a pattern for manufacturing a membrane on a second surface of the insulating substrate;

forming the membrane on the first surface by an etching process and solvent treatment on the second surface of the insulating substrate;

removing the formed membrane;

stacking a graphene layer on the hollow structure formed at a portion from which the membrane of the first surface is removed;

forming the resonance unit by treating a surface exposed to an outside of the graphene layer with a surface treatment agent containing the functional group; and coupling the detection unit to the resonance unit including the functional group.

In the present invention, the electrode is not limited as long as the electrode inhibits the achievement of the object of the nano-dynamic system of the present invention, but at least one of gold (Au), palladium (Pd), platinum (Pt), silver (Ag), copper (Cu), aluminum (Al), nickel (Ni), chromium (Cr), and titanium (Ti) may be used, or two or more metals may be used in combination. For example, one consisting of a Au or Ar layer and a Cr layer may be used and one in which the gold (Au) layer is stacked on the chromium (Cr) layer may be used. In this case, the sensitivity and accuracy of the mass sensor may be improved due to the very low resistance.

In addition, in the present invention, various methods can be used without any limitations to put and immobilize the prepared graphene on the hollow structure, and as one specific example, may include plasma treatment, and more specifically, the graphene prepared by being cured at 30 to 70° C. and then subjected to oxygen plasma treatment can be immobilized to the hollow structure without gaps.

Since graphene, which belongs to carbon nanomaterials, has high mobility, low electrical noise (1/f noise), and a two-dimensional structure in which all carbon atoms are exposed to the atmosphere, the graphene has a very wide surface area compared to the existing organic/inorganic materials, and as a result, has the advantage of maximizing the sensitivity when applied to the sensor. In addition, when the graphene having the two-dimensional structure is subjected to a lithography process to be made into an element, the graphene can be more easily and conveniently surface-functionalized than other 0-dimensional or 1-dimensional structures having a large surface area to give a function that can detect various kinds of gases, and the graphene can be driven even with low power consumption due to excellent electrical characteristics of the graphene.

Examples of the graphene may include, but is not limited to, graphene mechanically exfoliated from graphite, graphene chemically exfoliated from graphite, graphene chemically synthesized from a carbon source, graphene synthesized from a SiC substrate, and the like.

In the present invention, the graphene may be the platform of the sensor element by the patterning process. The patterning process may include, but is not limited to, reactive ion etching (RIE), photolithography, electron-beam lithography, scanning probe lithography, laser-induced direct patterning, block copolymer lithography, nanoimprint lithography, photocatalytic etching, plasma etching processes, and the like.

The metal electrode may be deposited by at least one selected from electron-beam evaporation deposition, thermal evaporation deposition, laser molecular beam epitaxy (L-MBE), pulsed laser deposition (PLD), electro-plating, and sputtering, but the deposition method is not limited thereto.

The patterning in the present invention is not limited at a level that does not hinder the object of the present invention, and may be carried out using any suitable lithography process, for example, any one or two or more selected from the group consisting of photolithography, electron-beam lithography, ion-beam lithography, EUV lithography, and x-ray lithography, but may be preferably carried out using photolithography.

In the present invention, the hollow structure is not limited at a level that does not hinder the object of the present invention, but preferably has an inner area completely applied by the graphene layer.

In the present invention, the kind of the insulating substrate is not limited as long as the insulating substrate does not hinder the object of the present invention. For example, the silicone substrate or one in which the $SiO_2$ layer and the $SiN_x$ layer (x is a real number between 1 and 5) are sequentially stacked on both surfaces of the silicon substrate may be used. The range of x is not particularly limited within the range in which the object of the invention is not hindered, but preferably a real number between 1 and 5, more preferably a real number between 1 and 3, and most preferably a real number between 1 and 2, and for example, x=4/3. In the case of using the material within the above range, in forming the membrane followed by forming the hollow structure used for the attachment of graphene devices, the hollow structure can be stably processed in a shorter time without loss, and the sensor having excellent sensitivity can be manufactured.

In the present invention, in the case of the insulating substrate in which the $SiO_2$ layer and the $SiN_x$ layer are sequentially stacked on both surfaces of the silicon substrate, as long as the object of the present invention is not hindered, the forming of the membrane may include, for example, etching the $SiN_x$ layer on the second surface of the insulating substrate by a reactive ion etching process; and removing the $SiO_2$ layer and etching the silicon substrate to form a $SiN_x$ membrane on the first surface of the insulating substrate.

Through the above steps, the graphene layer connected to the resonance unit may not only be easily attached to the hollow structure by sequentially removing the insulating layer from the second surface, but the Q-factor of the device may also have a value between $10^4$ and $10^5$ which is the high range of the ranges that semiconductors generally have, so the graphene can be used for the sensor having high sensitivity, and therefore is very preferable.

In the present invention, the method used in the etching process of the silicon substrate is not particularly limited within the range in which the object of the present invention is not hindered, and dry or wet etching may be used without limitation. For example, a method for treating acid, base, salts thereof, azole-based compounds, plasma, or a mixture thereof, and the like may be used, and particularly, in one specific example of the present invention, potassium hydroxide (KOH), which is a base having a concentration of 10 to 40 wt %, is used to configure the nano-dynamic device, thereby more easily forming the membrane.

Hereinafter, the content of the present invention will be described in more detail with reference to Examples. Examples are only for explaining in more detail the present invention, but the scope of the present invention is not limited thereto.

EXAMPLE 1

Fabricating of Nano-Structure Having Hollow

Coating Photoresist on Wafer

In order to fabricate a silicon oxide film through-hole, a wafer (manufactured by Unisill Technology Co., Ltd., South Korea) in which $SiO_2$ and $Si_3N_4$ layers are sequentially stacked on both surfaces of a silicon substrate was used. Photoresist AZ 9260 (MicroChemicals GmbH, Germany) was spin-coated on the wafer at 4000 rpm for 40 seconds and then cured at 115° C. for 3 minutes.

As described above, the photoresist-coated wafer was covered with a metal mask (Soda Lime/Chrome mask manufactured by LMTEC Co.) using MA/BA6 contact aligner (Suss MicroTec) and was exposed to an energy of 900 $mJ/cm^2$.

Generation of Electrode on Front Surface of Wafer

The photoresist on the front surface of the exposed wafer was etched using developer AZ 726 MIF (Microchemicals GmbH, Germany). The front surface of the wafer, which has been subjected to the typical photolithography process, was deposited with a 20 nm chromium (Cr) layer using an e-beam evaporator and then deposited with a 100 nm Au layer. Thereafter, the wafer was immersed in acetone to complete the electrode.

Manufacturing of the Membrane Structure

A membrane pattern for manufacturing a membrane was prepared on a back surface of a photoresist-coated wafer by the typical photolithography process. Thereafter, $Si_3N_4$ was etched by flowing 23% of potassium hydroxide (KOH) at 80° C. using a reactive ion etching apparatus. Thereafter, the $SiO_2$ layer was removed at 80° C. using a buffered oxide etchant (BOE) solution. The silicon substrate was etched by flowing 23% of potassium hydroxide (KOH). Since a thickness of the silicon substrate is about 500 μm, it took about 10 hours to leave the $Si_3N_4$ membrane on the opposite side.

By doing so, the $Si_3N_4$ membrane having a size of about 25 μm×25 μm was manufactured before applying suspended graphene, and then the $Si_3N_4$ membrane was removed by the dry etching to form a hollow.

EXAMPLE 2

Formation of Suspended Graphene on Nano-Structure

Preparation of Graphene

Graphene for fabricating a nano-dynamic device based on suspended graphene was prepared by the following dry exfoliation method.

First, coordinates were engraved on a 300 nm silicon oxide substrate by a wet etching method. After the surface is cleaned, a poly (styrene sulfonic acid) (PSS) which is a water-soluble polymer was coated, and then a poly (methyl methacrylate) (PMMA), (manufactured by Sigma Aldrich Co.) layer was uniformly spin-coated.

Thereafter, graphite (NGS Naturgraphit GmbH, Leinburg, Germany) attached to 3M tape (3M) adhered to the surface of the substrate to prepare graphene.

Movement of Graphene to Nano-Structure

The prepared graphene was moved through the following procedure so as to completely cover the graphene on the hollow structure formed through the removal of the $Si_3N_4$ membrane in Example 1.

Graphene specimens to which OHP hold having a window adhered were slightly floated in deionized water to dissolve the coated PSS. When a Si substrate and a graphene-PMMA film are separated, the graphene film was picked up from the deionized water, exactly placed on the nano-structure having the hollow structure while checking a location to move using a microscope, and cured at 50° C. to have a strong fixing force. Thereafter, the graphene film was cured at 180° C. for 2 minutes to remove the PMMA on the graphene surface and was subjected to oxygen plasma treatment. Subsequently, the graphene film was immersed in a PG remover (MicroChem) at 60° C. for 2 hours to completely remove the PMMA. Finally, in order to prevent the deformation of the graphene due to surface tension, the graphene film was treated with a critical point dryer (CPD).

FIG. 3 shows an optical image of the nano-dynamic device after placing the graphene on the substrate having the hollow structure according to the present invention and a result of measuring Raman spectrum.

A horizontal axis of the Raman spectrum shows a Raman shift and a vertical axis thereof shows intensity in arbitrary unit. It could be confirmed that after the graphene is placed on the substrate, a D band is generated in the vicinity of 1350 $cm^{-1}$, a G band is generated in the vicinity of 1600 $cm^{-1}$, and a 2D band is generated at 2700 $cm^{-1}$. In addition, it was confirmed that the graphene exists in two or more layers by calculating a full width at half maximums (FWHMs) which is a difference between two independent variable values that are half a maximum value of a function.

EXAMPLE 3

Characteristics of Nano-Dynamic Device with Graphene Layer

In order to measure kinetic characteristics of a nano-dynamic device fabricated by the above embodiment, a room temperature laser reflection measurement system as shown in the schematic diagram of FIG. 2 was used.

The laser reflection measurement system is an apparatus that scans a helium-neon (He—Ne) laser on a surface of a dynamic device and measures the number of photons reflected from the surface of the dynamic device using a photo detection unit by measuring the movement of the dynamic device, and in this example, the biomolecules were detected and measured while checking the degree of vacuum at room temperature.

It was measured whether the nano-dynamic device is suitable for the detection of biomolecules using the apparatus of the same principle as the schematic diagram of FIG. 2. As a result, as shown in FIG. 4A, it was confirmed that the measured resonance frequency was about 16.367 MHz and the Q-factor is about 14,613. The Q-factor achieved to date in semiconductor nanoelectromechanical systems (NEMS) ranges from $10^3$ to $10^5$, and considering the above range, it was confirmed that the nano-dynamic device according to the present invention is a device that has a relatively high Q-factor, that is, high sensitivity to a change in mass.

In addition, as can be seen in FIG. 4B, as a result of driving the nano-dynamic device with different intensities of 10 decibel milliwattes (dBm) to 15 dBm, it was confirmed that since the measured amplitude decreases as the driving strength increases, nonlinearity is observed. The observation of the nonlinearity is an important basis for confirming that the output signal is due to the resonance of the dynamic device. In the figure, it was confirmed that the nonlinearity is observed when the driving strength increases to 14 dB or more.

EXAMPLE 4

Nano-Dynamic System (Biosensor) for Virus Detection Using Nano-Dynamic Device

N-hydroxysuccinimidyl pyrenbutanoate (manufactured by Sigma-Aldrich Co.) was mixed with dimethylformamide (DMF) (manufactured by Sigma-Aldrich Co.) to prepare a 6 mM succinimidyl ester solution.

The solution was dripped to the surface of the graphene, and after 3 hours, molecules that failed to react with the DMF were removed. The surface of the graphene with 50 mM of tris buffer solution (pH 7.4; Sigma-Aldrich Co.) was washed and then the solution was dripped for about 10 minutes.

After 10 minutes, 10 nM of vaccinia virus antibody (Korea Advanced Institute of Science and Technology) solution was dripped for 6 hours. In this case, the antibody was immobilized in a non-covalent bond manner using a pyrene group of succinimidyl ester.

Thereafter, vaccinia viruses at a concentration of $10^8$ plaque forming unit (PFU), $10^5$ PFU, and $10^3$ PFU were each bound to the immobilized antibody for 1 hour at room temperature and were washed with deionized water to remove the unbounded viruses and salts contained in the buffer solution which can affect the measurement results, and then the varying resonance frequency was measured.

FIG. 5 shows the results of the detection by the nano-dynamic system according to the concentration of the vaccinia virus. As can be seen from FIG. 4, it can be seen that the resonance frequency value of the graphene changes significantly as each chemical treatment process proceeds, and it was confirmed that as the molecules adsorbed to the surface of the graphene increase, the resonance frequency is gradually downshifted. Also, it was confirmed that as the concentration of the vaccinia virus is lowered from $10^8$ PFU to $10^5$ PFU and then $10^3$ PFU, a shift width of the resonance frequency gradually decreases.

On the other hand, it could be seen that the variation width of the resonance frequency due to the linker molecule and the virus antibody in which the concentration is kept constant have similar values in the results for three virus concentrations. In the case of the linker molecule and the viral antibody, the variation in the resonance frequency was $4.93\pm2.84$ MHz and $3.51\pm1.28$ MHz, respectively, as a result of three repeated experiments. As the concentration decreases from $10^8$ PFU to $10^5$ PFU and then $10^3$ PFU, the shift width of the resonance frequency was measured at 14.7 MHz, 1.94 MHz, and 0.04 MHz, respectively. This is the phenomenon occurring as the amount of virus in contact with the surface of the nano-dynamic system decreases.

COMPARATIVE EXAMPLE 1

In Example 4 above, except that 10 μM of botulinum toxin molecule (BoNT/E) was bound to the nano-dynamic system instead of vaccinia virus, other procedures was the same to measure the variation width of the resonant frequency.

As a result, as can be seen in the lower right diagram of FIG. 5, it can be seen that the shift of the resonance frequency does not appear at all, which means that the nano-dynamic system (biosensor) manufactured by being bound to the vaccinia virus antibody in Example 4 is selectively bound only to the vaccinia virus.

EXAMPLE 5

Analysis of Surface to which Virus Molecule is Adsorbed

For analysis of vaccinia virus adsorbed to the surface of the nano-dynamic system, the analysis of the surface of the vaccinia virus of $10^5$ PFU that contacts the nano-dynamic system in the above Examples was performed by X-ray photoelectron spectroscopy (XPS) and scanning electron microscope (SEM).

A change in a ratio of carbon (C), oxygen (O), and nitrogen (N) was measured by the XPS every time different molecules are adsorbed to the surface of the graphene.

TABLE 1

| Unit % | | | | |
|---|---|---|---|---|
| | Graphene | Linker molecule | Vaccinia virus antibody | Vaccinia virus |
| Carbon (%) | 64.43 | 54.61 | 67.06 | 53.58 |
| Oxygen (%) | 21.02 | 27.71 | 16.63 | 24.99 |
| Nitrogen (%) | — | 1.04 | 7.6 | 11.89 |

As a result, it was confirmed that when the linker molecule was introduced to the graphene surface, the content of nitrogen increases, and when the vaccinia virus comes into contact with the antibody, the contents of nitrogen and oxygen increase greatly.

EXAMPLE 6

Estimation of Mass Value in Contact with Nano-Dynamic System

Through the above Examples, it could be confirmed that as the loading mass is added on the graphene, the resonant frequency is downshifted. Based on this, the mass value in contact with the nano-dynamic system was estimated through an equation that has been used in a conventional scientific field.

$$\delta m \sim 2\, M_{eff}/\omega_o\, \delta\omega \quad \text{[Equation I]}$$

δm: mass added to nano-dynamic device, $M_{eff}$: effective mass of nano-dynamic device, $\omega_o$: resonance frequency of nano-dynamic device, and δω: change in resonance frequency of nano-dynamic device The density of the graphene obtained from the graphite of the present invention is reported to be $7.4\times10^{-7}$ kg/m$^2$, and the thickness of the monolayer graphene is 3.35 Å. Based on this, the obtained effective mass of the mass sensor is $2.6\times10^{-15}$ kg.

As a result, the mass of the vaccinia virus used in the present invention is as follows.

TABLE 2

| Experimental group (Concentration of vaccinia virus) | Effective mass of mass sensor | Resonance frequency | Variation in resonance frequency | Mass of adsorbed vaccinia virus | Number of adsorbed vaccinia viruses |
|---|---|---|---|---|---|
| $10^8$ PFU | $2.6 \times 10^{-15}$ kg | 16.367 MHz | 14.7 MHz | $87.82 \times 10^{-13}$ g | 1317 |
| $10^5$ PFU | | | 1.94 MHz | $27.94 \times 10^{-13}$ g | 419 |
| $10^3$ PFU | | | 0.04 MHz | $0.75 \times 10^{-13}$ g | 11.25 |

* At this time, the number of adsorbed vaccinia viruses is a result calculated by taking the average mass of mature vaccinia viruses at about 7.5 femtograms (fg; $10^{-15}$ g).

As can be seen in the results of Table 2, the nano-dynamic system of the present invention was confirmed that the mass detection in units of $10^{-15}$ g was achieved to complete the present invention.

The nano-dynamic system developed by the present invention is based on the dynamic properties of pure graphene itself, and the main technical feature of the present invention is to implement the resonator type biosensor and is to detect the biomolecules in a short time without any chemical treatment. In addition, there is an advantage of detecting molecules that do not have electrical properties, and there is an important feature that is less likely to cause errors because the molecular bonding process on the surface of the graphene is simple.

The invention claimed is:

1. A fabrication method for a biosensor, comprising:

applying a photoresist on an insulating substrate;

exposing a first surface of the insulating substrate, etching the photoresist, and then forming an electrode;

forming a pattern for manufacturing a membrane on a second surface of the insulating substrate;

forming the membrane on the first surface by an etching process and solvent treatment on the second surface of the insulating substrate;

removing the formed membrane;

stacking a graphene-polymer layer on a hollow structure formed at a portion from which the membrane of the first surface is removed, wherein the graphene-polymer layer is exactly placed on the hollow structure while checking the location of the graphene-polymer layer relative to the hollow structure;

curing the graphene in the graphene-polymer layer by heat treatment of the graphene at 30-70° C. to fix the graphene on the hollow structure;

further heat treating the graphene-polymer layer to at least 180° C. to remove the polymer from the graphene-polymer layer, thereby leaving a cured graphene layer;

subjecting the cured graphene to oxygen plasma treatment to further fix and immobilize the cured graphene layer on the hollow structure without gaps;

forming a resonance unit by treating a surface exposed to an outside of the graphene layer with a surface treatment agent containing a functional group; and coupling a detection unit to the resonance unit including the functional group, and wherein the insulating substrate has a $SiO_2$ layer and a $SiN_x$ layer which are sequentially stacked on both surfaces of the insulating substrate, and x is a real number between 1 and 5, and wherein an inner area of the hollow structure is $6.0\times10^2$ $\mu m^2$ to $6.3\times10^2$ $\mu m^2$.

2. The fabrication method of claim 1, wherein the electrode has a gold (Au) layer that is stacked on a chromium (Cr) layer.

3. The fabrication method of claim 1, wherein the hollow structure has an inner area completely applied by the graphene layer.

4. The fabrication method of claim 1, wherein the forming of the membrane when the insulating substrate has the $SiO_2$ layer and the $SiN_x$ layer that are sequentially stacked on the insulating substrate includes:

etching the $SiN_x$ layer on the second surface of the insulating substrate by a reactive ion etching process; and removing the $SiO_2$ layer and etching the silicon substrate to form a $SiN_x$ membrane on the first surface of the insulating substrate.

5. The fabrication method of claim 1, wherein in the etching of the insulating substrate, wet etching using 10 to 40 wt % of base is used.

6. The method of claim 1, wherein the polymer in the graphene polymer layer is poly (methyl methacrylate) (PMMA).

* * * * *